United States Patent
Brucher et al.

(10) Patent No.: US 6,344,024 B1
(45) Date of Patent: Feb. 5, 2002

(54) MULTIFREQUENCY ULTRASOUND PROBE

(75) Inventors: Rainer Brucher, Lonsee; Achim Wiest; Gerold Widenhorn, both of Überlingen, all of (DE)

(73) Assignee: DWL Elektronische Systeme GmbH (DE)

( * ) Notice: Subject to any disclaimer, the term of this patent is extended or adjusted under 35 U.S.C. 154(b) by 0 days.

(21) Appl. No.: 09/423,700
(22) PCT Filed: May 12, 1998
(86) PCT No.: PCT/EP98/02771
§ 371 Date: Jan. 21, 2000
§ 102(e) Date: Jan. 21, 2000
(87) PCT Pub. No.: WO98/52068
PCT Pub. Date: Nov. 19, 1998

(30) Foreign Application Priority Data

May 12, 1997 (DE) .................................... 297 08 338 U

(51) Int. Cl.⁷ ................................................ A61B 8/14
(52) U.S. Cl. ...................................................... 600/459
(58) Field of Search ................................ 600/437, 443, 600/447, 448, 449, 458, 459; 367/7, 11, 103; 73/625, 626, 602

(56) References Cited

U.S. PATENT DOCUMENTS

| 2,645,727 A | 7/1953 | Willard |
| 4,459,853 A | 7/1984 | Miwa et al. |
| 4,841,977 A | 6/1989 | Griffith et al. |
| 4,872,346 A | 10/1989 | Kelly-Fry et al. |
| 5,327,893 A | * 7/1994 | Savic .......................... 600/454 |
| 5,348,015 A | 9/1994 | Moehring et al. |
| 5,357,964 A | * 10/1994 | Spivey et al. ................ 600/455 |
| 5,410,205 A | 4/1995 | Gururaja |
| 5,549,111 A | * 8/1996 | Wright et al. ................ 600/555 |

FOREIGN PATENT DOCUMENTS

| DE | 30 08 553 A1 | 9/1980 |
| DE | 34 41 563 A1 | 5/1985 |
| GB | 1 266 143 | 3/1972 |

* cited by examiner

*Primary Examiner*—Marvin M. Lateef
*Assistant Examiner*—Ali M. Imam
(74) *Attorney, Agent, or Firm*—Piper Marbury Rudnick & Wolfe

(57) ABSTRACT

The invention relates to an ultrasound probe for use especially in medical diagnostics using ultrasonography. Said probe comprises an ultrasound sensor configured to generate an ultrasound send signal as a reaction to an electrical impulse and to receiving a receive signal reflected on an observation medium. Said ultrasound sensor is held in a supporting device and fitted with coupling and transmission devices for sending the transmission signal into the observation medium. Said transmission signal is a multifrequency signal comprising at least two individual signals which are separate from each other in the frequency range. Said probe also comprises means to evaluate the reflected receive signal in relation to the individual signals. The ultrasound sensor has a single crystal for generating signals, which crystal is simultaneously and in a synchronized manner impinged upon by the multifrequency signal with several carrier frequencies in the proximity of its resonance frequency. On a back surface facing away from the observation medium, the single crystal has an adaptation element made of metal or glass which serves to influence the band width and/or resonance frequency in a predeterminable manner.

8 Claims, 3 Drawing Sheets

MULTIFREQUENCY ULTRASOUND PROBE

Figure 1:
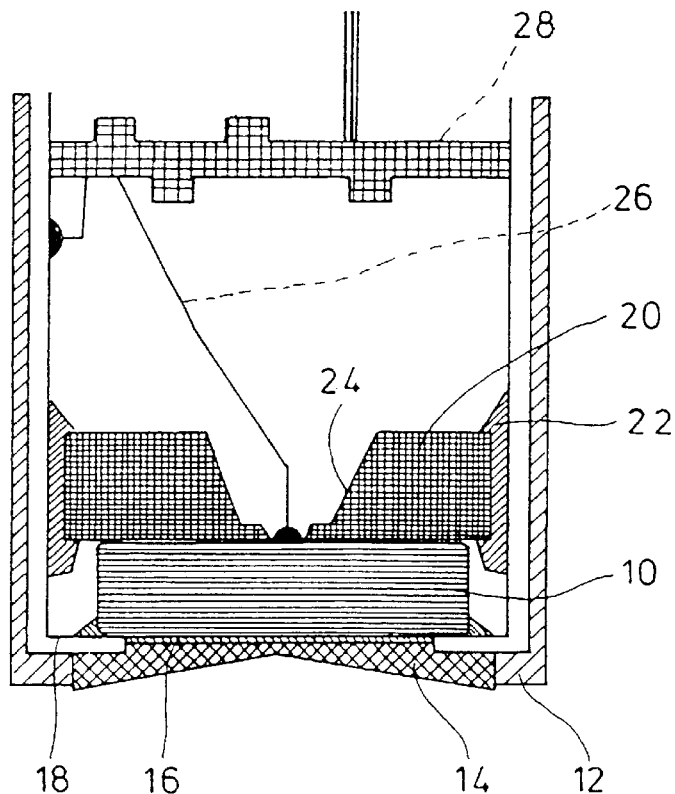

The present invention concerns an ultrasonic probe as set forth in the classifying portion of claim 1.

There are numerous possible uses for apparatuses of that kind in medical diagnostics, in particular in ultrasonic sonography. Thus, ultrasonic probes are used in particular in connection with medical ultrasonic apparatuses which are based on the Doppler principle and which generate ultrasonic signals which are suitable for a respective diagnostic purpose in the range of between about 1 and about 20 MHz. The ultrasonic probes are also adapted to (individual) frequencies of that kind in a corresponding manner.

Ultrasonic probes which are known from the state of the art usually consist of a piezoelectric crystal which is suitably electrically stimulated in order then to produce an ultrasonic signal, for example 2, 4, 8 or 16 MHz, the crystal having geometrical and electrical parameters which are intended for a respective frequency.

If there is then the intention in the context of diagnostic purposes to change the frequency, for example from 2 to 4 MHz or from 2 to 2.5 MHz, then the ultrasonic probe used is usually replaced by a probe which is appropriate suited to the new frequency band.

Particularly in the technical area of embolism detection by means of ultrasound, a new and medically significant area of use of transcranial Doppler sonography, there is the technical challenge of reliably and distinguishably detecting the occurrence of embolisms in a blood vessel which is monitored by means of ultrasound, an embolism in that respect being distinguished by reflection properties of the incident ultrasonic signal, that are characteristic in relation to the surrounding blood. It will of course be noted that it is still difficult to draw a distinction between true embolisms and (undesired) interference effects, for example artefacts which occur due to probe movement.

It has been found that in particular embolisms can be recognised and distinguished in addition by characteristic, frequency-dependent reflection properties of one or more incident ultrasonic signals, in which case for example the reflected signal at a first ultrasonic frequency can be markedly higher or lower than the corresponding reflected signal level at a second frequency.

For uses of that kind or other diagnostic ultrasonic uses in which an important aspect is substantially simultaneous introduction of a plurality of ultrasonic frequencies into an observation medium or an observation object, there are hitherto practically no suitable probe arrangements. On the contrary, the procedure adopted usually involves managing with a plurality of individual probes which are secured to a common carrier or supporting arrangement. Apart from mechanical difficulties or difficulties involved in coupling procedures however there is here in particular the problem of focusing the respective signals from the individual probes on a common observation point, for example at a location in a blood vessel, while problems in terms of adjustment and accuracy are obvious.

Therefore the object of the present invention is to provide an ultrasonic probe of the general kind set forth, which is suitable for simple and user-friendly multifrequency operation, that is to say which can simultaneously irradiate more than one ultrasonic frequency (or a coherent ultrasonic band) on to a focus point in the observation medium and receive the signal reflected therefrom.

That object is attained by the ultrasonic probe as set forth in claims 1, 2, 3 and 7 respectively.

Advantageously in that respect—due to the structural and geometrical unit of the single crystals involved or, in the case of the structure set forth in claim 1, only the one crystal—optimum, coincident focusing of the simultaneously irradiated, narrow-band carrier signals is always achieved, and in particular adjustment operations or setting operations by an operator are no longer required.

In addition it is possible in the manner according to the invention to produce an extremely compact probe which, both in terms of production and also in terms of practical use, exhibits marked advantages in regard to portability and operation.

In otherwise known manner the received reflected Doppler signal is then passed—preferably in multi-channel mode—to an evaluation operation which can then be adapted in particular also for frequency- (pattern-) dependent embolism detection.

In that respect basically the ultrasonic probe according to the invention is suitable for any media to be monitored, without in any way being limited to blood vessels.

An essential feature of the invention also provides that the multifrequency signal for the ultrasonic sensor is a simultaneous and synchronised multifrequency signal, wherein the individual carrier frequencies are preferably in a non-harmonic relationship with each other.

Advantageous developments of the invention are described in the appendant claims.

It is thus particularly preferable for the single crystals which are disposed in mutually adjacent relationship in the coupling means to be so provided in a common introduction plane as to afford the desirable square shape each comprising two pairs of single crystals.

Both series and also parallel resonance apply as the resonance frequency in accordance with the invention, both for this embodiment and also for the further configurations of the invention.

Figure 2:
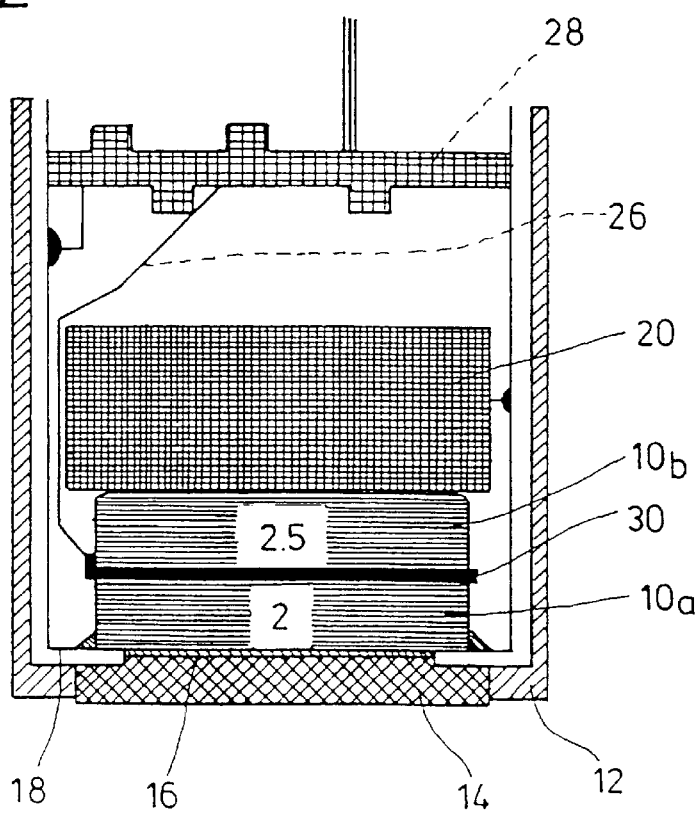
Figure 3:
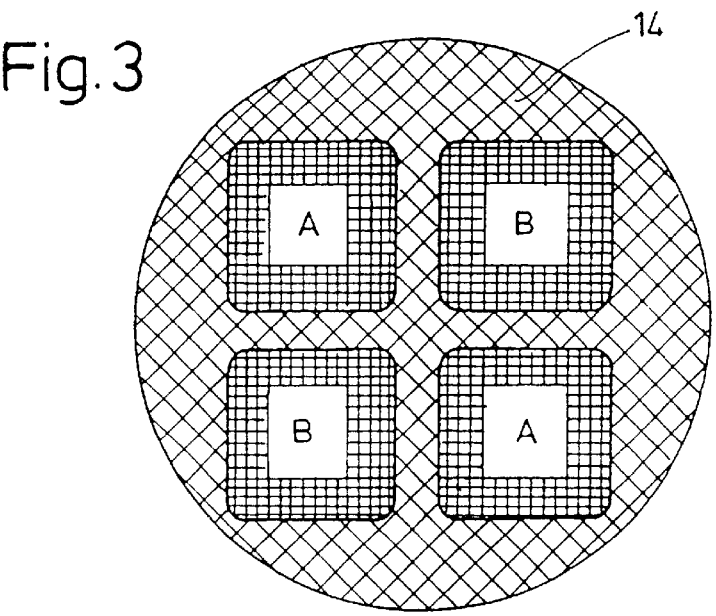
Figure 4:
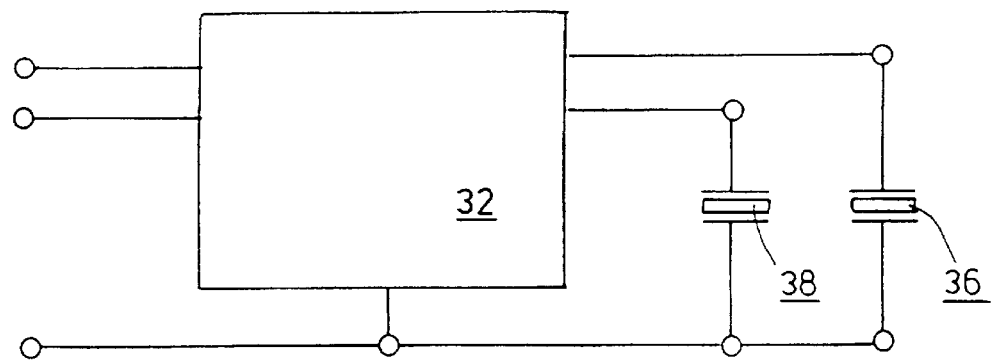
Figure 4:
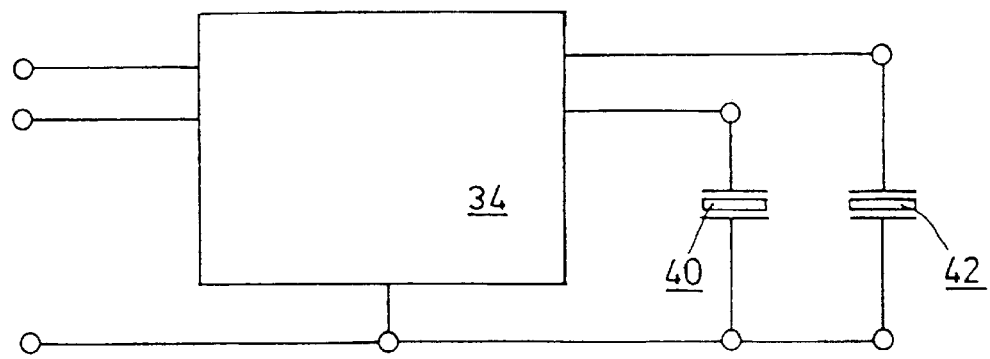
Figure 5:
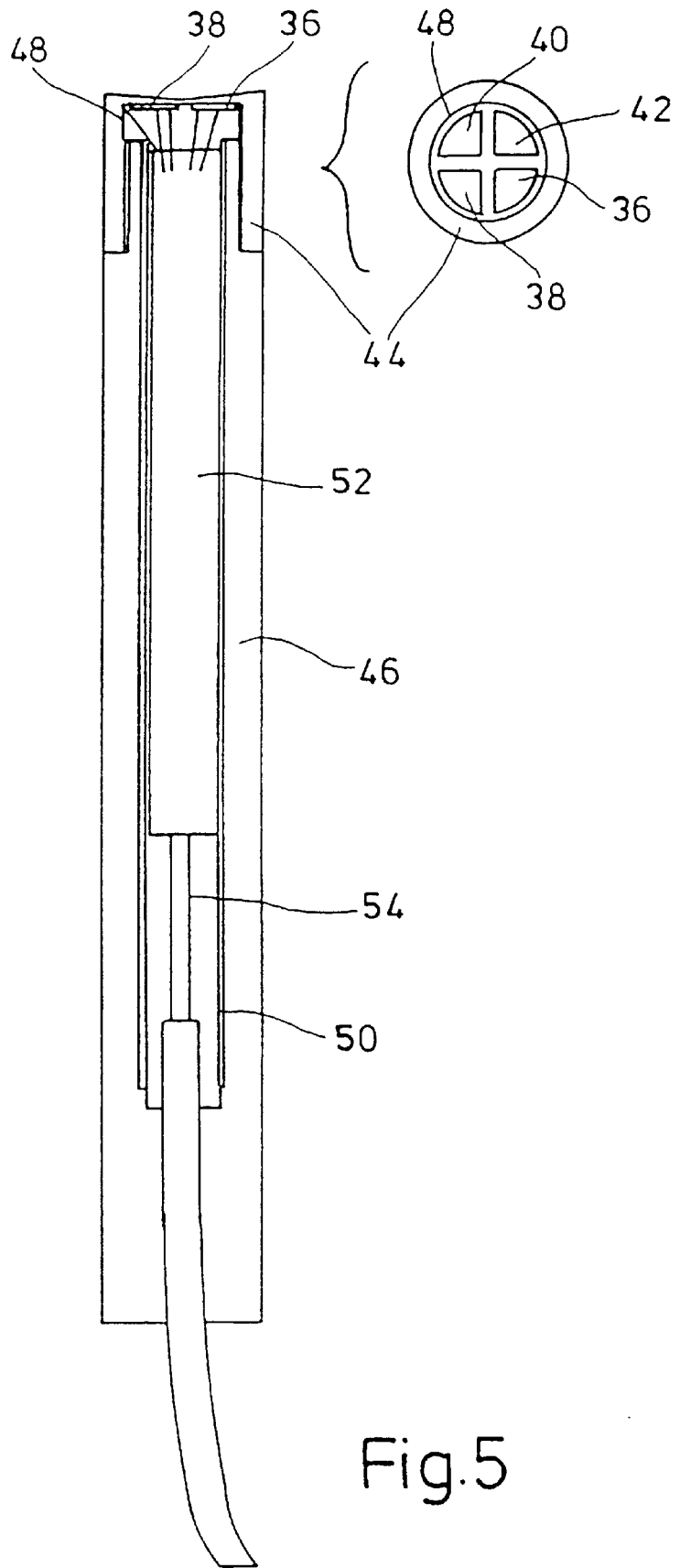

Further advantages, features and details of the invention will be apparent from the totality of the present application documents, not limited to specifically illustrated combinations, but in any conceivable combination of the illustrated individual features, and from the accompanying drawings in which:

FIG. 1 is a side view in section of an ultrasonic probe according to the invention in a first preferred embodiment thereof, FIG. 2 is a side view of an ultrasonic probe according to the invention in a second embodiment thereof, FIG. 3 is a plan view of the coupling or introduction surface of an ultrasonic probe according to the invention in a third embodiment thereof, FIG. 4 shows a block circuit diagram of a multifrequency ultrasonic probe in accordance with a further embodiment of the invention, for which protection is claimed independently in the context of the present disclosure, and FIG. 5 shows a sectional side view of this further multifrequency ultrasonic probe.

FIG. 1 shows a first embodiment of the ultrasonic probe according to the invention (best mode). A piezoelectric crystal 10 whose resonance frequencies (series and parallel resonance frequency) is set to the range between 2 and 2.5 MHz covers the bottom opening of a cup-shaped plastic housing 6. The bottom opening thereof is additionally closed off by a lens element 14 of suitable plastic material, which is circular—corresponding to the cylindrical crystal 10—and which is intended to serve for the—focusing or non-focusing—coupling of the ultrasonic oscillations of the piezoelectric crystal 10 into a body to be monitored. The endeavour in this respect is that the foci of both frequencies are as coincident as possible for embolism detection, in particular in regard to intensity distribution.

Provided between the crystal 10 and the lens 14 is a thin adhesive layer 16, preferably of silver conductive adhesive, of a thickness in the range of a few micrometers, for coupling purposes.

In addition in the internal region of the housing 12 it is lined with a screening internal housing 18, preferably of copper material. Laterally secured to the screening casing 18 is not only the piezoelectric crystal 10 but also an adaptation or backing element 20 of metal or glass which is provided on the crystal in opposite relationship to the lens 14 and which is secured to the casing 18 by means of radially peripherally extending adhesive 22. The backing element 20 has a substantially central bore 24 which is conical in the illustrated embodiment, which has a central opening to the surface of the crystal 10, and which is dimensioned in accordance with the desired resonance frequency or band width (quality) of the piezoelectric crystal 10. Also engaging through that central opening is a signal line 26 which electrically connects the crystal 10 to an amplifier unit 28, symbolically indicated by a printed circuit board.

In the illustrated embodiment the amplifier 28 is in the form of a two-channel amplifier unit with two parallel channels in order to be able to process the respective individual frequencies—2 MHz and 2.5 MHz—and pass them on for further evaluation.

The specific dimensions of the crystal 10, the backing element 20 and the choice of material thereof—preferably metal or glass—are dependent on the respectively desired resonance frequencies or an intended band width which must be sufficiently wide to be able to irradiate the synchronised transmission frequencies in the desired manner.

In accordance with the invention therefore the quality of an ultrasonic piezoelectric crystal is deliberately reduced by this embodiment, thereby increasing the band width thereof (for the multifrequency). Technically, this is achieved by the particularly associated, rearward adaptation (backing), whereby in spite of this single crystal probe it then becomes multifrequency-capable.

Reference will now be made to FIG. 2 to describe an alternative embodiment of the invention. Identical references are used herein for elements or functional groups corresponding to those in FIG. 1.

Unlike the single crystal structure shown in FIG. 1, the embodiment of FIG. 2 uses a pair of crystals 10a, 10b in the illustrated laminate or sandwich structure, wherein the crystal 10a which is at the front in the irradiation direction is designed for the resonance frequency of 2 MHz and the rear crystal 10b is designed for the frequency of 2.5 MHz. The two crystals are connected by a silver electrode 30 covering the entire surface area, which serves for feeding and removing signals by means of a feed line 26 to the amplifier unit 28. In the illustrated embodiment the backing element 20 covers the entire surface area and does not have a bore and, in comparison with FIG. 1, it does not have an edge adhesive join to the screening cup 18.

The probe illustrated in FIG. 2 is therefore based on the principle of single crystals which are arranged in succession in space and which by virtue of a suitable backing are adapted for joint irradiation of both frequencies into the observation medium. The plastic lens 14 shown in FIG. 2 is also designed as a necessary criterion in accordance with the specific adaptation or matching conditions (in contrast to the embodiment of FIG. 1 in which it can be designed to be both focusing and also non-focusing).

The embodiment of FIG. 2 also provides that the specific dimensioning of the resonators and the backing element are governed by the respectively required resonance conditions.

The embodiment shown in FIG. 3 is based on the so-called 'mosaic principle'; a plurality of individual crystals are arranged in the introduction surface—the surface of the lens 14 which is in contact with the object to be observed—in a regular or irregular pattern, wherein each of the illustrated crystals A, B has the respective transmission frequency (A: crystal with a 2 MHz resonance frequency, B: crystal with a 2.5 MHz resonance frequency) as the resonance frequency. In the illustrated embodiment therefore two crystals are disposed on each resonance frequency—arranged in a square.

In this case, the various ultrasonic irradiation characteristics are to be as coincident as possible in a depth region of about 40 mm to about 80 mm, that is to say they are to provide for as good a focusing effect as possible. Such a crystal array with single crystals is then designed in such a fashion that the respective crystals on the lens have an individual angle of inclination so that the irradiation effects meet at the desired (depthwise) region.

It is also provided that the respective single crystals have contacting means and can be provided with individual backing elements for tuning of the resonance frequency.

It is also possible for the illustrated array to be of a variable configuration without in any way being restricted to the illustrated square shape.

The illustrated embodiment thus provides for transmission and reception of two different central frequencies (here by way of example: 2 MHz and 2.5 MHz) by means of a single probe which then in particular can also be preferably used for frequency-discriminating analysis of Doppler ultrasonic signals which are reflected at embolisms or other bodies in the flow of blood. The fixed association of the respective, resonance-forming oscillating bodies in the probe means that there is no need for expensive manual setting by an operator, nor is there any expectation of inaccuracies which are caused for example by focus requirements and which were disadvantageously noted in relation to the state of the art.

FIG. 4 shows the block circuit diagram of a multifrequency ultrasonic probe for blood flow measuring devices for which protection is claimed independently in the context of the present disclosure. This probe which is also shown in FIG. 5 as a side view in section can be used both for continuous (CW) and also for pulsating (PW) ultrasonic operation and it can be simultaneously operated at a plurality of frequencies. The illustrated embodiment shows the version for 4 and 8 MHz. At these frequencies which are given by way of example, the probe is suitable in particular for measurement in vessels at a depth of 0 cm to about 4–6 cm, wherein the measurements can be implemented both transcranially (on the head) and also at peripheral vessels (for example neck, arms, legs).

FIG. 4 shows a pair of preamplifiers 32, 34 which are associated with the respective frequency ranges of 8 and 4 MHz respectively, more precisely, the preamplifier 32 is connected to an 8 MHz reception piezoelectric element 36 and to a transmission piezoelectric element 38 for that frequency range, while the preamplifier 34 is connected to transmission and reception piezoelectric crystals 40 and 42 respectively. FIG. 5 shows the arrangement of the piezoelectric elements 36 through 42 in the head of the probe: a probe capsule 44 at the intervention end of a probe housing 46 forms a substantially cylindrical sleeve; in the end face thereof, under a (plastic) ultrasonic lens, the four piezoelectric elements 36 through 42—each in the form of a segment in the shape of a quarter of a circle—are assembled together to form a substantially circular overall surface, wherein the individual crystal segments are separated from each other by thin bars or webs. The arrangement is enclosed by an upper screening tube 48 which is fitted over a wire connection to ground, precisely like a lower screening tube 50.

The amplifier electronics shown in FIG. 4 is accommodated in an elongated amplifier housing 52 in the middle of the housing 46 and is supplied by way of a feed cable 54.

The illustrated structure thus affords a very easily handleable multifrequency arrangement which provides a plurality of piezoelectric crystals—separated from each other—in compact form at the engagement end so that the specific depth of penetration for the simultaneously irradiated ultrasonic waves is as small as possible and thus the focusing effect is correspondingly accurate.

Furthermore it is advantageously provided that the probe capsule 44 has at its end an incorporated lens for focusing of the ultrasonic beam, for example in the slightly conical configuration shown in FIG. 5, so that focusing of the ultrasonic waves on to a central focal point in the observation medium can be effected.

In addition this embodiment may also be the subject of variations for example in accordance with further features described with reference to FIGS. 1 through 3.

What is claimed is:

1. An ultrasonic probe, in particular for uses in the area of medical diagnostics by means of ultrasonic sonography, comprising an ultrasonic. Sensor (10: 10*a*, 10*b*, A, B) which is adapted to produce an ultrasonic transmission signal as a reaction to an electrical stimulation and to receive a reception signal reflected at an observation medium and which is held in a carrier arrangement (12) and which is provided with coupling and transmission means (14) for coupling the transmission signal into the observation medium, characterised in that the transmission signal is a multifrequency signal comprising at least two individual signals which are spaced from each other in the frequency range and having two carrier frequencies which are in a non-harmonic relationship to each other and focused into a common point in the observation medium by a common lens, and there are provided means for evaluation of the reflected reception signal in dependence on the individual signals, wherein the ultrasonic sensor has a single crystal (10) for signal production, which is simultaneously and synchronisedly acted upon with the multifrequency signal with a plurality of carrier frequencies in the proximity of its resonance frequency and is provided on a rearward surface remote from the observation medium with an adaptation element (20) of metal or glass for influencing the band width and/or the resonance frequency in a predeterminable manner.

2. An ultrasonic probe, in particular for uses in the area of medical diagnostics by means of ultrasonic sonography, comprising an ultrasonic sensor (10: 10*a*, 10*b*, A, B) which is adapted to produce an ultrasonic transmission signal as a reaction to an electrical stimulation and to receive a reception signal reflected at an observation medium and which is held in a carrier arrangement (12) and which is provided with coupling and transmission means (14) for coupling the transmission signal into the observation medium, characterised in that the transmission signal is a multifrequency signal comprising at least two simultaneous and synchronised individual signals spaced from each other in the frequency range and having a non-harmonic relationship to each other, with respective carrier frequencies, and focused into a common point in the observation medium by a common lens, and there are provided means for evaluation of the reflected reception signal in dependence on the individual signals, wherein the ultrasonic sensor has a sandwich arrangement of a plurality of single crystals (10*a*, 10*b*), preferably in accordance with the number of individual signals, which are arranged lying in surface contact one upon the other in an irradiation direction, and the sandwich arrangement is provided at a rearward surface remote from the observation medium with an adaptation element (20) of metal or glass.

3. An ultrasonic probe as set forth in claim 2 characterised in that there are provided four piezoelectric crystals which are arranged in a square with respect to an introduction surface of the coupling means and which are adapted in pairs to two resonance frequencies.

4. An ultrasonic probe as set forth in claim 3 characterised in that the piezoelectric crystals have a respective angle of inclination of their main radiation direction with respect to an introduction surface of the coupling means, which is respectively so set that the respective transmission signals of the piezoelectric crystals focus in a coincident relationship at a predetermined depth in the observation medium.

5. An ultrasonic probe as set forth in claim 4 characterised in that the predetermined depth in the observation medium is between 40 and 80 mm.

6. An ultrasonic probe, in particular for uses in the area of medical diagnostics by means of ultrasonic sonography, comprising an ultrasonic sensor (38–42) which is adapted to produce a multifrequency ultrasonic transmission signal having two carrier frequencies which are in a non-harmonic relationship to each other as a reaction to an electrical stimulation and to receive a reception signal reflected at an observation medium and which is held in a carrier arrangement (46) and which is provided with coupling and transmission means (44) for coupling the transmission signal into the observation medium, characterised in that the ultrasonic sensor has a plurality of single crystals for signal generation, which at the end form a common continuous introduction surface for the ultrasonic signals and which are arranged in mutually adjacent relationship under a common lens element.

7. An ultrasonic probe as set forth in claim 6 characterised in that the ultrasonic sensor has two single crystals at the transmission end and two single crystals at the reception end, for two frequency ranges, which are in the shape of segments of circles in the introduction surface.

8. An ultrasonic probe as set forth in claim 6 characterised in that the multifrequency signal has the carrier frequencies of 2 and 2.5 MHz or the carrier frequencies of 1.7 and 2.4 MHz.

\* \* \* \* \*